United States Patent

Kirstgen et al.

Patent Number: 5,294,639
Date of Patent: Mar. 15, 1994

[54] α-ARYLACRYLIC ACID DERIVATIVES, THEIR PREPARATION AND THEIR USE FOR CONTROLLING PESTS AND FUNGI

[75] Inventors: Reinhard Kirstgen, Neustadt; Albrecht Harreus, Ludwigshafen; Uwe Kardorff, Mannheim; Thomas Kuekenhoehner, Frankenthal; Harald Rang, Ludwigshafen; Gisela Lorenz, Neustadt; Eberhard Ammermann, Ludwigshafen; Christoph Kuenast, Otterstadt, all of Fed. Rep. of Germany

[73] Assignee: BASF Aktiengesellschaft, Ludwigshafen, Fed. Rep. of Germany

[21] Appl. No.: 754,850

[22] Filed: Sep. 4, 1991

[30] Foreign Application Priority Data

Sep. 7, 1990 [DE] Fed. Rep. of Germany ....... 4028391

[51] Int. Cl.$^5$ ................ C07C 69/612; C07C 69/618; A01N 37/10; A01N 37/34
[52] U.S. Cl. .................... 514/522; 514/538; 514/539; 514/543; 558/414; 560/9; 560/10; 560/19; 560/21; 560/56; 560/59; 560/60
[58] Field of Search ............ 560/60, 59, 56, 9, 10, 560/19, 21; 514/522, 538, 539, 543; 558/414

[56] References Cited

U.S. PATENT DOCUMENTS

| | | | |
|---|---|---|---|
| 4,723,034 | 2/1988 | Schirmer et al. | 560/60 |
| 4,782,177 | 11/1988 | Schirmer et al. | 560/60 |
| 4,857,545 | 8/1989 | Anthony et al. | 514/452 |
| 4,937,372 | 6/1990 | Wenderoth et al. | 560/55 |
| 5,021,581 | 6/1991 | Clough et al. | 546/309 |

FOREIGN PATENT DOCUMENTS

| | | | |
|---|---|---|---|
| 31625/89 | 10/1989 | Austria | 514/469 |
| 2193495A | 2/1988 | United Kingdom | 514/364 |

Primary Examiner—Alan L. Rotman
Attorney, Agent, or Firm—Keil & Weinkauf

[57] ABSTRACT

Abstract of the Disclosure: α-Arylacrylic acid derivatives of the general formula I

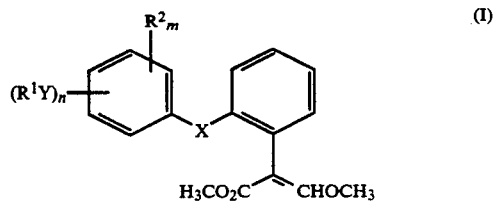

where
X is ethylene or ethenylene;
Y is a direct bond or oxygen;
$R^1$ is an unsubstituted or substituted mononuclear or dinuclear aromatic or heteroaromatic system;
$R^2$ is cyano, nitro, halogen, alkyl, haloalkyl, alkoxy, haloalkoxy, alkylthio or haloalkylthio;
n is 1 or 2, and the radicals may be different if n is 2, and
(c m is 0, 1 or 2, and the radicals may be different if m is 2,
with the proviso that $R^1$ is not phenyl when n is 1 and m is 0, their preparation, insecticides and fungicides containing them and methods for their use.

4 Claims, No Drawings

α-ARYLACRYLIC ACID DERIVATIVES, THEIR PREPARATION AND THEIR USE FOR CONTROLLING PESTS AND FUNGI

The present invention relates to α-arylacrylic acid derivatives of the general formula I

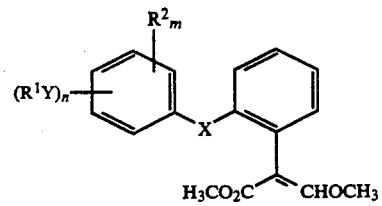

where
X is ethylene or ethenylene;
Y is a direct bond or oxygen;
$R^1$ is a mononuclear or dinuclear aromatic system which is bonded via a carbon atom and, in addition to carbon members, may contain from one to four nitrogen atoms or one or two nitrogen atoms and/or an oxygen or a sulfur atom, and this aromatic system may carry from one to seven halogen atoms and/or from one to four of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-haloalkylthio, $C_3$–$C_6$-cycloalkyl, $C_5$- or $C_6$-cyclo-alkenyl, $C_2$–$C_4$-alkenyl or $C_2$–$C_4$-alkynyl; $R^2$ is cyano, nitro, halogen, $C_1$–$C_4$-alkyl, $C_1$–$C_4$-haloalkyl, $C_1$–$C_4$-alkoxy,, $C_1$–$C_4$-haloalkoxy, $C_1$–$C_4$-alkythio or $C_1$–$C_4$-haloalkylthio;
n is 1 or 2, and the radicals may be different if n is 2;
m is 0, 1 or 2, and the radicals may be different if m is 2, with the proviso that $R^1$ is not phenyl when n is 1 and m is 0.

The present invention furthermore relates to processes for the preparation of these compounds I, agents containing them and methods for controlling pests with the aid of α-arylacrylic acid derivatives of the general formula I'

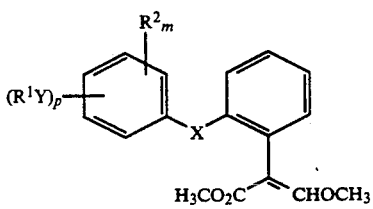

where $R^1$, $R^2$, X, Y and m have the abovementioned meanings and p is 1 or 2, with the proviso that $R^1$ may also be phenyl if X is ethylene, Y is oxygen, p is 1 and m is 0, and methods for controlling fungi with the aid of α-arylacrylic acid derivatives of the general formula I.

The literature discloses α-arylacrylic acid derivatives as fungicides (EP-A 203 606 and EP-A 229 974), as insecticides and fungicides (EP-A 178 826) and as insecticides (EP-A 256 667 and EP-A 335 519).

It is an object of the present invention to provide novel effective insecticides and fungicides.

We have found that this object is achieved by the α-arylacrylic acid derivatives I defined at the outset. We have also found processes for the preparation of these α-arylacrylic acid derivatives and agents containing them and methods for their use.

The α-arylacrylic acid derivatives I are obtainable, for example, by the methods described in the literature cited. They are particularly advantageously obtained by one of the processes A, B and C described below.

Process A

The α-arylacrylic acid derivatives of the formula I in which X is ethenylene are obtained, for example, by reacting a phosphonic acid of the general formula II with a benzaldehyde of the general formula III in a conventional manner (eg. EP-A 203 606; J. Am. Chem. Soc. 83 (1961), 1732) in an inert organic solvent in the presence of a base.

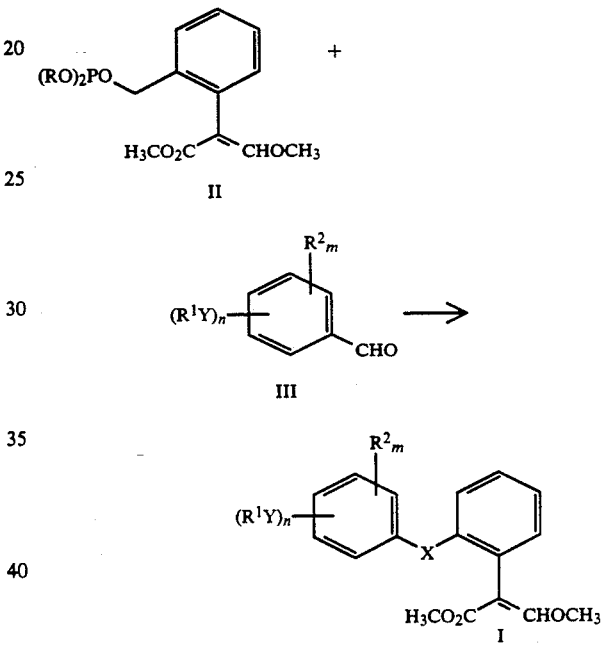

In formula II, R is $C_1$–$C_8$-alkyl, in particular methyl, ethyl, propyl or 1-methylethyl.

The reaction is carried out in general at $-30°$ to $60°$ C., preferably from $0°$ to $40°$ C.

Examples of suitable solvents are diethyl ether, benzene, toluene, tetrahydrofuran, dimethoxyethane, methanol, ethanol and dimethylformamide.

Tetrahydrofuran and dimethylformamide are particularly suitable.

Bases used in this process are n-butyllithium, sodium hydride, sodium methylate, potassium tert-butylate, sodium tert-amylate, lithium dimethylamide and lithium bistrimethylsilylamide.

The preparation of the intermediates required is described, for example, in the literature cited at the outset.

Process B

The α-arylacrylic acid derivatives of the formula I in which X is ethenylene are obtained, for example, by reacting a phosphonic acid of the general formula IV with a benzaldehyde of the formula V in a conventional manner in an inert organic solvent in the presence of a base.

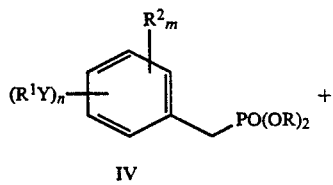

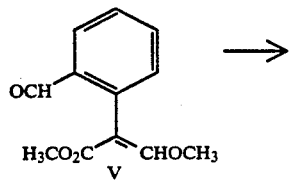

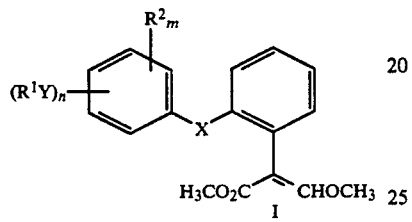

In formula IV, R is $C_1$–$C_8$-alkyl, in particular methyl, ethyl, propyl or 1-methylethyl.

The reaction is carried out in general at from −30° to 60° C., preferably from 0° to 40° C.

Suitable solvents and bases in general and in particular are those stated in the case of process A.

The preparation of the intermediates required is described in, for example, Houben-Weyl, Vol. XII/L, page 433 et seq. (1963).

Process C

The α-arylacrylic acid derivatives of the formula I in which X is ethylene are obtained, f or example, by reducing a compound of the general formula I in which X is ethenylene in a conventional manner (Houben-Weyl, Vol. V/2b, 264–267 (1981); Houben-Weyl, Vol. IV/1c, 580 et seq. (1980); J. Am. Chem. Soc. 83 (1961), 4302 et seq.) in an inert organic solvent.

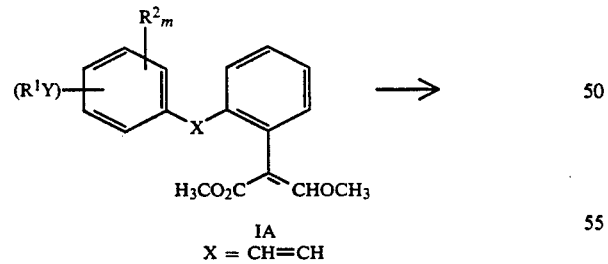

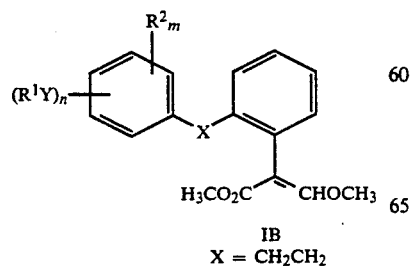

The reaction is carried out in general at from 0° to 100° C., preferably from 20° to 40° C.

Examples of suitable solvents are acetic acid, ethanol, ethyl acetate and tetrahydrofuran or corresponding mixtures.

Examples of suitable reducing agents are hydrogen in the presence of noble metal catalysts, such as Pd, Pd/CaCO$_3$, Pd/C, Pt at a hydrogen pressure of from 1 to 10 bar or diamine which is produced in situ from hydrazine and oxygen in the presence of Cu(II) ions.

In view of the intended use of the compounds I in insecticides and fungicides, suitable substituents and indices are the following:

X is ethylene (—CH$_2$—CH$_2$—) or ethenylene (—CH=CH—)

Y is a direct bond or oxygen;

R$^1$ is a mononuclear or dinuclear aromatic system which is bonded via a carbon atom and, in addition to carbon members, may contain from one to four nitrogen atoms or 1 or 2 nitrogen atoms and an oxygen or sulfur atom, such as phenyl, naphthyl, 2-pyrryl, 3-pyrryl, 3-pyrazolyl, 4-pyrazolyl, 5-pyrazolyl, 2-imidazolyl, 4-imidazolyl, 5-imidazolyl, 1,2,4-triazol-3-yl, 1,2,4-triazol-5-yl, 2-pyridyl, 3-pyridyl, 4-pyridyl, 2-pyrimidyl, 4-pyrimidyl, 5-pyrimidyl, 2-pyrazinyl, 3-pyrazinyl, 1,3,5-triazin-2-yl, 3-indolyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,3,4-oxadiazol-2-yl, 1,3,4-thiadiazol-2-yl, 2-benzoxazolyl or 2-benzothiazolyl, where this aromatic system may carry from one to seven halogen atoms, such as f luorine, chlorine, bromine or iodine, in particular fluorine or chlorine, and/or from one to four of the following radicals: cyano, nitro;

$C_1$–$C_4$-alkyl, such as methyl, ethyl, propyl, 1-methylethyl, butyl, 1-methylpropyl, 2-methylpropyl or 1,1-dimethylethyl, in particular methyl, ethyl, 1-methylethyl or 1, 1-dimethylethyl;

$C_1$–$C_4$-haloalkyl, in particular Cl- or C2-haloalkyl, such as chloromethyl, dichloromethyl, trichloromethyl, fluoro-methyl, difluoromethyl, trifluoromethyl, chlorofluoro-methyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy;

$C_1$–$C_4$-haloalkoxy, in particular $C_1$–or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, 1,1,2,2-tetrafluoroethoxy or pentafluoroethoxy, in particular trifluoromethoxy, 1,1,2,2-tetrafluoroethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

$C_1$–$C_4$ haloalkythio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoromethylthio;

$C_3$–$C_6$-cycloalkyl, such as cyclopropyl, cyclobutyl, cyclopentyl or cyclohexyl, preferably cyclopropyl or cyclopentyl;

$C_5$- or $C_6$-cycloalkenyl, such as cyclopent-1-enyl, cyclopent-2-enyl, cyclopent-3-enyl, cyclohex-1-enyl, cyclohex-2-enyl or cyclohex-3-enyl, preferably cyclopent-2-enyl or cyclopent-3-enyl;

$C_2$–$C_4$-alkenyl, such as ethenyl, 1-propenyl, 2-propenyl, 1-methylethenyl, 1-butenyl, 2-buteny 1-propenyl, 2-methyl-1-propenyl, 1-methyl-2-propenyl or 2-methyl-2-propenyl, preferably ethenyl or 1-propenyl; or $C_2$–$C_4$-alkynyl, such as ethynyl, 1-propynyl, 2-propynyl, 1-butynyl, 2-butynyl, 3-butynyl or 1-methyl-2-propynyl, preferably ethynyl or 1-propynyl; $R^2$ is cyano, nitro, halogen;

$C_1$–$C_4$-alkyl, such as methyl, ethyl, propyl, 1-methylethyl, butyl, 1-methylpropyl, 2-methylpropyl or 1,1-dimethylethyl, in particular methyl, ethyl, 1-methylethyl or 1,1-dimethylethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoromethylthio;

n is 1 or 2, and the radicals may be different if n is 2, and m is 0, 1 or 2, and the radicals may be different if m is 2, with the proviso that $R^1$ is not phenyl when n is 1 and m is 0.

Depending on the starting materials used and on the reaction conditions, the compounds I can of course be obtained both in the form of pure structural isomers and in the form of isomer pairs or in the form of isomer mixtures and can be used in these forms as active ingredients. Isomer mixtures or isomer pairs can be separated into the sterically pure components in a conventional manner. The biological activity is dependent on the steric configuration of the compounds in specific cases.

Examples of particularly preferred α-arylacrylic acid derivatives of the general formula IA or IB are shown in the Table below.

TABLE

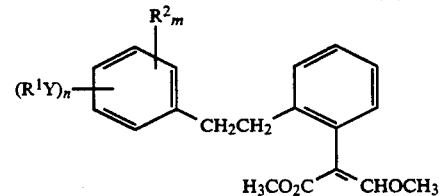

(IA)

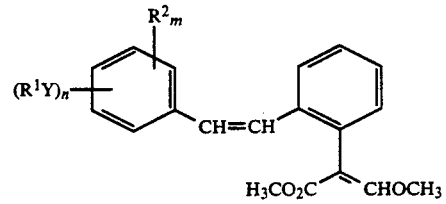

(IB)

| $(R^1Y)_n$ | $R^2_m$ |
|---|---|
| 3-Phenyl | 2-CH$_3$ |
| 3-Phenyl | 2-F |
| 3-Phenyl | 2-Cl |
| 3-Phenyl | 2-Br |
| 3-Phenyl | 2-C$_2$H$_5$ |
| 3-Phenyl | 2-CH=CH$_2$ |
| 3-Phenyl | 2-CF$_3$ |
| 3-Phenyl | 2-OCH$_3$ |
| 3-Phenyl | 2-CN |
| 3-Phenyl | 2-NO$_2$ |
| 3-Phenyl | 4-CH$_3$ |
| 3-Phenyl | 4-Cl |
| 3-Phenyl | 4-F |
| 3-Phenyl | 6-CH$_3$ |
| 3-Phenyl | 6-Cl |
| 3-Phenyl | 6-F |
| 3-Phenyl | 5-Cl |
| 3-Phenyl | 5-F |
| 3-(3-F-Phenyl) | 2-CH$_3$ |
| 3-(2-CH$_3$-Phenyl) | 2-CH$_3$ |
| 3-Phenyl | 2,4-F$_2$ |
| 3-Phenyl | 2,4-Cl$_2$ |
| 3-Phenyl | 2,4-(CH$_3$)$_2$ |
| 3-Phenyl | 2,6-F$_2$ |
| 3-(2-F-Phenyl) | H |
| 3-(2-Cl-Phenyl) | H |
| 3-(2-CH$_3$-Phenyl) | H |
| 3-(3-F-Phenyl) | H |
| 3-(3-Cl-Phenyl) | H |
| 3-(3-CH$_3$-Phenyl) | H |
| 3-(3-NO$_3$-Phenyl) | H |

TABLE-continued

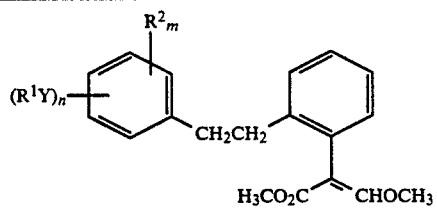 (IA)

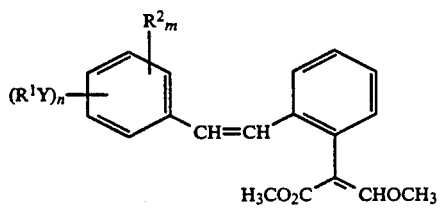 (IB)

| (R¹Y)ₙ | R²ₘ |
|---|---|
| 3-(3-CH₃O-Phenyl) | H |
| 3-(3,5-Cl₂-Phenyl) | H |
| 3-(4-F-Phenyl) | H |
| 3-(4-Cl-Phenyl) | H |
| 3-(4-CH₃-Phenyl) | H |
| 3-(4-CN-Phenyl) | H |
| 3-(3-CN-Phenyl) | H |
| 3-(4-NO₂-Phenyl) | H |
| 3-(4-MeO-Phenyl) | H |
| 4-(2-CH₃-Phenyl) | H |
| 4-(2-Cl-Phenyl) | H |
| 4-(3-Cl-Phenyl) | H |
| 4-(3-CH₃-Phenyl) | H |
| 4-(3-CH₃O-Phenyl) | H |
| 4-(3-F-Phenyl) | H |
| 4-(2,5-(CH₃O)₂-Phenyl) | H |
| 4-(2,5-(CH₃O)₂-Phenyl) | 3-Cl |
| 4-(2,5-(CH₃O)₂-Phenyl) | 3-Br |
| 4-(2,5-(CH₃O)₂-Phenyl) | 2,3,6-Cl₃ |
| 4-(4-CH₃-Phenyl) | H |
| 4-(4-CH₃O-Phenyl) | H |
| 4-(4-C₂H₅-Phenyl) | H |
| 4-(4-F-Phenyl) | H |
| 4-(4-Cl-Phenyl) | H |
| 4-(2,4-(Cl-Phenyl) | H |
| 4-(2,6-(Cl-4-CH₃-Phenyl) | 2,6-Cl₂ |
| 4-(3-CN-Phenyl) | H |
| 4-(4-CN-Phenyl) | H |
| 4-(3-NO₂-Phenyl) | H |
| 4-(4-NO₂-Phenyl) | H |
| 3-(4-Cl-Phenoxy) | H |
| 3-(3-Cl-Phenoxy) | H |
| 3-(4-CF₃-Phenyxy) | H |
| 3-(3-CF₃-Phenoxy) | H |
| 3-(4-CH₃O-Phenoxy) | H |
| 3-(3-CH₃O-Phenoxy) | H |
| 3-(4-CH₃-Phenoxy) | H |
| 3-(3-CH₃-Phenoxy) | H |
| 3-(4-tC₄H₉-Phenoxy) | H |
| 3-(3,4-(Cl₂-Phenoxy) | H |
| 3-(3,5-(Cl₂-Phenoxy) | H |
| 3-(2,5-Cl₂, 3-CF₃-Phenoxy) | 2-Cl |
| 3-(2-Cl, 5-F, 3-CF₃-Phenoxy) | 2-Cl |
| 3-(2,5-Cl₂, 3-CF₃-Phenoxy) | 2-Br |
| 3-(2-Cl, 5-F, 3-CF₃-Phenoxy) | 2-Br |
| 3-(2,5-Cl₂, 3-CF₃-Phenoxy) | 2-CN |
| 3-(2-Cl, 5-F, 3-CF₃-Phenoxy) | 2-CN |
| 4-Phenoxy | H |
| 4-(4-CH₃-Phenoxy) | H |
| 4-(3-CH₃-Phenoxy) | H |
| 4-(4-C₂H₅-Phenoxy) | H |
| 4-(3-C₂H₅-Phenoxy) | H |
| 4-(4-tC₄H₉-Phenoxy) | H |
| 4-(3-tC₄H₉-Phenoxy) | H |
| 4-(4-CF₃-Phenoxy) | H |
| 4-(3-CF₃-Phenoxy) | H |
| 4-(4-Cl-Phenoxy) | H |
| 4-(3-Cl-Phenoxy) | H |
| 4-(4-Br-Phenoxy) | H |

TABLE-continued

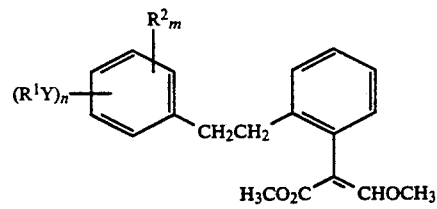 (IA)

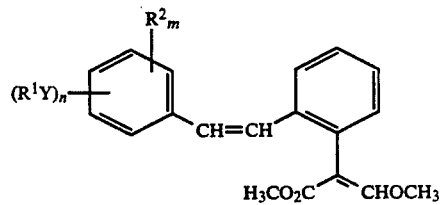 (IB)

| (R¹Y)ₙ | R²ₘ |
|---|---|
| 4-(3-Br-Phenoxy) | H |
| 4-(4-F-Phenoxy) | H |
| 4-(3-F-Phenoxy) | H |
| 4-(4-CH₃O-Phenoxy) | H |
| 4-(3-CH₃O-Phenoxy) | H |
| 4-(4-Phenoxyphenoxy) | H |
| 4-(2,3-Cl₂-Phenoxy) | H |
| 4-(3,4-Cl₂-Phenoxy) | H |
| 4-(2,5-Cl₂-Phenoxy) | H |
| 4-(3,5-Cl₂-Phenoxy) | H |
| 4-(3,5-Cl₂-Phenoxy) | H |
| 4-(3-Cl, 4-F-Phenoxy) | H |
| 4-(2-Cl, 4-CH₃-Phenoxy) | H |
| 4-(4-tC₄H₉-Phenoxy) | H |
| 4-Phenoxy | 3-F |
| 4-(3-Cl-Phenoxy) | 3-Cl |
| 4-(3-Br-Phenoxy) | 3-Cl |
| 4-(Pyrid-2-yl) | H |
| 3-(Pyrid-2-yl) | H |
| 4-(Pyrid-3-yl) | H |
| 3-(Pyrid-3-yl) | H |
| 4-(5-CF₃-Pyrid-2-yl) | H |
| 3-(5-CF₃-Pyrid-2-yl) | H |
| 4-(6-CF₃-Pyrid-2-yl) | H |
| 3-(6-CF₃-Pyrid-2-yl) | H |
| 4-(3-CH₃-Pyrid-2-yl) | H |
| 3-(3-CH₃-Pyrid-2-yl) | H |
| 4-(3-Cl, 5-CF₃-Pyrid-2-yl) | H |
| 3-(3-Cl, 5-CF₃-Pyrid-2-yl) | H |
| 4-(Pyridazin-3-yl) | H |
| 3-(Pyridazin-3-yl) | H |
| 4-(Pyrimid-2-yl) | H |
| 3-(Pyrimid-2-yl) | H |
| 4-(3-CF₃-Pyrid-2-yl) | H |
| 3-(3-CF₃-Pyrid-2-yl) | H |
| 4-(3,6-(CH₃-Pyrazin-2-yl) | H |
| 3-(3,6-(CH₃-Pyrazin-2-yl) | H |
| 4-(Pyrazin-2-yl) | H |
| 3-(Pyrazin-2-yl) | H |
| 4-(Pyrid-3-yl) | H |
| 3-(Pyrid-3-yl) | H |
| 4-(6-CF₃-Pyrid-2-yl) | H |
| 3-(6-CF₃-Pyrid-2-yl) | H |
| 4-(Thienyl-2-yl) | H |
| 3-(Thienyl-2-yl) | H |
| 4-(Thienyl-3-yl) | H |
| 3-(Thienyl-3-yl) | H |
| 4-(Thiazol-2-yl) | H |
| 3-(Thiazol-2-yl) | H |
| 4-(3-Cl-Thien-2-yl) | H |
| 3-(3-Cl-Thien-2-yl) | H |
| 4-(Furan-3-yl) | H |
| 3-(Furan-3-yl) | H |
| 4-(5-CH₃-Imidazol-4-yl) | H |
| 3-(5-CH₃-Imidazol-4-yl) | H |
| 4-(Triazol-2-yl) | H |
| 3-(Triazol-2-yl) | H |
| 4-(3-CH₃-1,2,4-Thiadiazol-5-yl) | H |
| 3-(3-CH₃-1,2,4-Thiadiazol-5-yl) | H |

TABLE-continued (IA)

$(R^1Y)_n$—[benzene ring]—$R^2_m$
$CH_2CH_2$—[benzene ring]—$C(H_3CO_2)=CHOCH_3$ (IB)

$(R^1Y)_n$—[benzene ring]—$R^2_m$
$CH=CH$—[benzene ring]—$C(H_3CO_2)=CHOCH_3$

| $(R^1Y)_n$ | $R^2_m$ |
|---|---|
| 4-(Isoxazol-5-yl) | H |
| 3-(Isoxazol-5-yl) | H |
| 4-(5-CH$_3$-Isoxazol-3-yl) | H |
| 3-(5-CH$_3$-Isoxazol-3-yl) | H |
| 4-(5-nC$_3$H$_7$-Isoxazol-3-yl) | H |
| 3-(5-nC$_3$H$_7$-Isoxazol-3-yl) | H |
| 4-Imidazolyl | H |
| 3-Phenyl | H |

The compounds of the formula I' are suitable for controlling pests from the class consisting of the insects, arachnids and nematodes. They can be used as pesticides in crop protection, in the hygiene and veterinary sectors and for the protection of stored materials.

The insect pests include, from the order of the butterflies (Lepidoptera), for example-*Agrotis ypsilon, Agrotis segetum., Alabama argillacea, Anticarsia gemmatalis, Argyresthia conjugella, Autographs gamma, Bupalus piniarius, Cacoecia murinana, Capua reticulana, Cheimatobia brumata,, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, gupoecilia ambiguella, Evetria bouliana, Feltia subterranea, Galleria mellonella, Grapholita funebrana, Grapholita molests, Heliothis armigera,, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absolute, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* from the order of the beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis,, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, onlema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria;* from the order of the Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestics, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* from the order of the Thysanoptera, for example *Frankliniella fusca, Frankliniella occidentalis, Frankliniella tritici, Scirtothrips citri, Thrips oryzae, Thrips palmi* and *Thrips tabaci;* from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata and Solenopsis invicta;* from the order of the Heteroptera, for example *Acrosternum hilare, Blisous leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis and Thyanta perditor;* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, macrosiphum avenae, Macrosiphum euphorbias, Macrosiphon rosae, Megoura viciae, Metopolophium dirhodum, Myzodes persicae, Myzus cerasi, Nilaparvata lugens, Pemphicjus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii;* from the order of the Isoptera, for example *Calotermes flavicollis, Leucotermes flavipes, Reticulitermes lucifugus* and *Termes natalensis;* from the order of the Orthoptera, for example *Acheta domestica, Blatta orientalis, Blatella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus*

*spretus, Nomadacris septemfasciata, Periplaneta americana, Schistocerca americana, Schistocerca peregrina, Stauronotus maroccanus* and *Tachycines asynamorus;* from the class of the Arachnoidea, for example Acarina, such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetrranychus carpini, Eriophyes sheldoni, Hyalomma truncatum, Ixodes ricinus, Ixodes rubicundus, Ornithodorus moubata, Otobins mecjnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae;* from the class of the nematodes, for example root gall nematodes, eg. *Meloidogyne hapla, Meloidogyne incognita* and *Meloidogyne javanica,* cyst-forming nematodes, eg. *Globodera rostochiensis, Heterodera avenae, Heterodera glycinae, Heterodera schatii, Heterodera triflolii,* and stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The compounds I are suitable as fungicides.

They possess excellent activity against a broad spectrum of phytopathogenic fungi, in particular from the class consisting of the Ascomycetes and Basidiomycetes. Some of them have systemic activity and can be used as foliage and soil fungicides.

They are particularly important for controlling a large number of fungi on various crops, such as wheat, rye, barley, oats, rice, corn, grass, cotton, soybean, coffee, sugar cane, grapevines, fruit trees and ornamental plants, vegetable plants, such as cucumbers, beans and cucurbitaceae, and on the seeds of these plants.

They are particularly suitable for controlling the following plant diseases:

*Erysiphe graminis* (powdery mildew) in cereals,
*Erysiphe cichoracearum* and *Sphaerotheca fuliginea* on cucurbitaceae,
Podosphaera leucotricha on apples,
*Uncinuld necator* on grapevines,
*Puccinia* species on cereals,
Rhizoctonia species on cotton and lawns,
Ustilago species on cereals and sugar cane,
*Venturia inaequalis* (scab) on apples,
Helminthosporium species on cereals,
*Septoria nodorum* on wheat,
*Botrytis cinerea* (gray mold) on strawberries and grapevines,
Cercospora arachidicola on peanuts,
Pseudocercosporella herpotrichoides on wheat and barley,
Pyricularia oryzae on rice,
Phytophthora infestans on potatoes and tomatoes,
Fusarium and Verticillium species on various plants,
*Plasmopara viticola* on grapevines and Alternaria species on vegetables and fruit.

The compounds are used by treating the fungi or the plants, seeds or materials to be protected from fungal attack or the soil with a fungicidal amount of the active ingredients. Application is effected before or after infection of the materials, plants or seeds by the fungi.

The active ingredients can be used as such, in the form of their formulations or in the application forms prepared therefrom, for example in the form of directly sprayable solutions, powders, suspensions or dispersions, emulsions, oil dispersions, pastes, dusting agents, broadcasting agents or granules, by spraying, atomizing, dusting, broadcasting or pouring. The application forms depend entirely on the intended uses; they should in any case ensure very fine distribution of the novel active ingredients.

For the preparation of directly sprayable solutions, emulsions, pastes or oil dispersions, mineral oil fractions having a medium to high boiling point, such as kerosene or diesel oil, and coal tar oils and oils of vegetable or animal origin, aliphatic, cyclic and aromatic hydrocarbons, eg. benzene, toluene, xylene, paraffin, tetrahydronaphthalene, alkylated naphthalenes or derivatives thereof, reethanol, ethanol, propanol, butanol, chloroform, carbon tetrachloride, cyclohexanol, cyclohexanone, chlorobenzene, isophorone and strongly polar solvents, eg. dimethylformamide, dimethyl sulfoxide, N-methylpyrrolidone and water, are suitable.

Aqueous application forms can be prepared from emulsion concentrates, pastes or wettable powders (spray powders, oil dispersions) by adding water. For the preparation of emulsions, pastes or oil dispersions, the substances as such or dissolved in an oil or solvent can be homogenized in water by means of wetting agents, adherents, dispersants or emulsifiers. However, it is also possible to prepare concentrates which consist of active substance, wetting agents, adherents, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylaryl sulfonates, alkyl sulfates, alkyl sulfonates, fatty alcohol sulfates and fatty acids and alkali metal and alkaline earth metal salts thereof, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active substances together with a solid carrier.

The formulations contain in general from 0.01 to 95, preferably from 0.1 to 90, % by weight of the active ingredient. The active ingredients are used in a purity of from 90 to 100%, preferably from 95 to 100% (according to NMR spectrum).

Examples of formulations are:

I. 5 parts by weight of compound No. 2.005 are thoroughly mixed with 95 parts by weight of finely divided kaolin. A dusting agent which contains 5% by weight of the active ingredient is obtained in this manner.

II. 30 parts by weight of compound No. 2.013 are thoroughly mixed with a mixture of 92 parts by weight of silica gel powder and 8 parts by weight of liquid paraffin which was sprayed onto the surface of this silica gel. A formulation of the active ingredient having good adhesion is obtained in this manner (active ingredient content 10, 23% by weight).

III. 10 parts by weight of compound No. 2.014 are dissolved in a mixture which consists of 90 parts by weight of xylene, 6 parts by weight of the adduct of from 8 to 10 moles of ethylene oxide with 1 mole of oleic acid N-monoethanolamide, 2 parts by weight of the calcium salt of dodecylbenzenesulfonic acid and 2 parts by weight of the adduct of 40 moles of ethylene oxide with 1 mole of castor oil (active ingredient content 9% by R weight).

IV. 20 parts by weight of compound No. 2.019 are dissolved in a mixture which consists of 60 parts by weight of cyclohexanone, 30 parts by weight of isobutanol, 5 parts by weight of the adduct of 7 moles of ethylene oxide with 1 mole of isooctylphenol and 5 parts by weight of the adduct of 40 moles of ethylene oxide with 1 mole of castor oil (active ingredient content 16% by weight).

V. 80 parts by weight of compound No. 2.016 are thoroughly mixed with 3 parts by weight of the sodium salt of diisobutylnaphthalene-alpha-sulfonic acid, 10 parts by weight of the sodium salt of a ligninsulfonic acid obtained from a sulfite waste liquor and 7 parts by weight of silica gel powder, and the mixture is milled in a hammer mill (active ingredient content 80% by weight).

VI. 90 parts by weight of compound No. 2.015 are mixed with 10 parts by weight of N-methyl-α-pyrrolidone, and a solution which is suitable for use in the form of very small drops is obtained (active ingredient content 90% by weight).

VII. 20 parts by weight of content No. 1.002 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with I mole of castor oil. By pouring the solution into 100,000 parts by weight of water and finely distributing it therein, an aqueous dispersion which contains 0.02% by weight of the active ingredient is obtained.

VIII. 20 parts by weight of active ingredient No. 1.005 are thoroughly mixed with 3 parts by weight of OCi. the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

Granules, for example coated,, impregnated and homogeneous granules, can be prepared by binding the active ingredients to solid carriers.

Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, eg. ammonium sulfate, ammonium phosphate, ammonium nitrate and ureas, and vegetable products, such as grain flours, bark meal, wood meal and nutshell meal, cellulosic powders and other solid carriers.

The active ingredient concentrations in the ready-to-use formulations can be varied within wide ranges.

In general, they are from 0.0001 to 10%, preferably from 0.01 to 1%.

The active ingredients can also be successfully used by the ultralow volume method (ULV), it being possible to apply formulations containing more than 95% by weight of active ingredient or even the active ingredient without additives.

The application rate of active ingredient for controlling insects is from 0.01 to 3, preferably from 0.05 to 1, kg/ha under open air conditions.

The application rates for fungicides are from 0.02 to 3 kg of active ingredient per ha, depending on the type of effect desired. The novel compounds can also be used in material protection (wood preservation), for example against Paecilomyces variotii.

In seed treatment, in general amounts of active ingredient of from 0.001 to 50 g, preferably from 0.01 to 10 g, per kilograin of seed are required.

Oils of various types, herbicides, fungicides, other pesticides and bactericides may be added to the active ingredients, if necessary immediately before use (tank mix). These agents can be mixed with the novel agents in a weight ratio of from 1 : 10 to 10 : 1.

Examples of Syntheses

The methods stated in the following Examples of Syntheses were used with appropriate modification of the starting compounds to obtain further compounds I. The compounds thus obtained are shown in the Table below, together with physical data.

EXAMPLES 2-(β-Methoxy-α-methoxycarbonylvinyl) -3'- (3 -trifluoromethyl)-phenoxystilbene 0.8 g of sodium hydride in 20 ml of absolute tetrahydrofuran (THF) is initially taken. A mixture of 7.9 g of dimethyl 2-(β-methoxy-α-methoxycarbonylvinyl)-benzylphosphonate and 7.3 g of 3-(3-trifluorophenoxy)-benzaldehyde in 100 ml of absolute THF is added dropwise at room temperature in the course of 30 minutes.

Stirring is carried out overnight and the reaction mixture is added to 200 ml of ice water and is extracted with 3 times 100 ml of tert-butyl methyl ether (MTBE). The organic phase is extracted 3 times by shaking with 100 ml of water each time and once by shaking with 100 ml of saturated NaCl solution. Drying is carried out over $MgSO_4$, after which the solvent is stripped off. The crude product (12.8 g) is purified over a silica gel column using toluene as the eluent. 8.8 g of a yellow oil (E/Z ratio 90 : 10) are obtained. (Active ingredient Example 2.006).

Methyl
α-(2-(3'-(3-trifluoromethyl]-phenoxy]-phenethyl-phenyl]-β-methoxyacrylate 2.7 g of 2- (β-methoxy-α-methoxycarbonylvinyl) -3'-(3-trifluoromethyl)-phenoxystilbene are hydrogenated at room temperature in 100 ml of THF in the presence of 1 g of 10% strength Pd/C at 0.05 bar excess hydrogen pressure. After the absorption of about 0.2 l of hydrogen in the course of 3 hours, the mixture is filtered and the filtrate is evaporated to dryness in a rotary evaporator. 2.5 g of a pale yellow oil are obtained. (Active ingredient Example 1.002).

2-(β-Methoxy-α-methoxycarbonylvinyl)-21-methyl-31-(3-fluorophenyl)-stilbene 0.75 g of sodium hydride in 100 ml of absolute THF is initially taken. A mixture of 7.5 g of dimethyl 2-(β-methoxy-α-methoxycarbonylvinyl)-benzylphosphonate and 5.1 g of 2-methyl-3-(3-fluorophenyl)-benzaldehyde in 0 ml of absolute THF is added dropwise at room temperature. Stirring is carried out overnight and the reaction mixture is added to ice water and is extracted with 3 times 100 ml of MTBE. The organic phase is extracted twice by shaking with 100 ml of saturated NaCl solution each time, dried over $Na_2SO_4$ and evaporated down. The crude product is purified over a silica gel column using 1 toluene/ethyl acetate as the eluent. 3.2 g of an oil (E/Z ratio 80 : 20) are obtained. (Active ingredient Example 2.004).

Methyl α-(2-(2'-methyl-31-[3-fluorophenyl])-phenethylphenyl]-β-methoxyacrylate 2 g of 2-([β-methoxy-α-methoxycarbonylvinyl)-2'-methyl-31-(3-fluorophenyl)-stilbene are hydrogenated at room temperature in 100 ml of THP in the presence of 1 g of 10% strength Pd/C at 0.3 bar excess hydrogen pressure. After 3 hours, the mixture is filtered and the filtrate is evaporated down to dryness in a rotary evaporator. 1.25 g of a solid are obtained. (Active ingredient Example 1.001).

TABLE 1

(IA)

[Structure showing $R^2_m$ substituted phenyl connected via $CH_2CH_2$ to phenyl with $H_3CO_2C$ and $CHOCH_3$ groups]

| No. | $(R^1Y)_n$ | $R^2_m$ | Phys. data [mp. (°C.); NMR (ppm)] |
|---|---|---|---|
| 1.001 | 3-(3-F-Phenyl) | 2-CH₃ | 72–79 |
| 1.002 | 3-(3-CF₃-Phenoxy) | H | 7.5(1H, 7.4–6.6(11H), 3.7(3H), 3.6(3H), 2.7(4H) |
| 1.003 | 3-(4-CH₃-Phenoxy) | H | 7.6(1H), 7.3–6.7(11H), 3.7(3H), 3.6(3H), 2.75(4H), 2.3(3H) |
| 1.004 | 3-(4-C(CH₃)₃-Phenoxy) | H | 7.5(1H), 7.3–6.7(11H), 3.7(3H, 3.6(3H), 2.7(4H), 1.15(9H) |
| 1.005 | 3-(3 5-Cl₂-Phenoxy) | H | 7.5(1H), 7.2–6.6(11H), 3.7(3H), 3.6(3H), 2.7(4H) |

TABLE 2

(IB)

[Structure showing $R^2_m$ substituted phenyl connected via $CH=CH$ to phenyl with $H_3CO_2C$ and $CHOCH_3$ groups]

| No. | $(R^1Y)_n$ | $R^2_m$ | Phys. data [mp. (°C.); NMR [ppm] |
|---|---|---|---|
| 2.001 | 3-Phenyl | 2-CH₃ | 7.8-7.0(14H); 6.3; 3.8 (3H); 3.7(3H); 2.15(3H) |
| 2.002 | 3-Phenyl | 2-F | 7.8-7.1(15H); 3.8(3H); 3.7(3H) |
| 2.003 | 3-Phenyl | 2-CF₃ | 7.8-7.1(14H); 6.95(1H); 3.8(3H); 3.7(3H) |
| 2.004 | 3-(3-F-Phenyl) | 2-CH₃ | 7.8-6.9(14H); 3.8(3H); 3.7(3H); 2.15(3H) |
| 2.005 | 3-(4-Cl-Phenoxy) | H | 7.6-6.7(15H); 3.7(3H); 3.6(3H) |
| 2.006 | 3-(3-CF₃-Phenoxy) | H | 7.7-6.8(15H); 3.7(3H); 3.6(3H) |
| 2.007 | 3-(4-CH₃O-Phenoxy) | H | 7.65-6.7(15H); 3.8(3H); 3.7(3H); 3.6(3H) |
| 2.008 | 3-(4-CH₃-Phenoxy) | H | 7.8-6.8(15H); 3.7(3H); 3.6(3H); 2.3(3H) |
| 2.009 | 3-(4-tC₄H₉-Phenoxy) | H | 7.7-6.8(15H); 3.7(3H); 3.6(3H); 1.3(9H) |
| 2.010 | 3-(3,4-Cl₂-Phenoxy) | H | 7.6-6.7(15H); 3.7(3H); 3.6(3H) |
| 2.011 | 3-(3,5-Cl₂-Phenoxy) | H | 7.6-6.7(15H); 3.75(3H); 3.65(3H) |
| 2.012 | 4-Phenoxy | H | 7.75(1H); 7.6(1H); 7.5-6.9(14H); 3.8(3H); 3.7(3H) |
| 2.013 | 4-(3-C₂H₅-Phenoxy) | H | 7.7(1H); 7.6(1H); 7.45-6.8(13H); 3.8(3H); 3.65(3H); 2.6(2H); 1.2(3H) |
| 2.014 | 4-(3-CF₃-Phenoxy) | H | 7.7(1H); 7.6(1H); 7.5-6.9(13H; 3.8(3H); 3.7(3H) |
| 2.015 | 4-(3-Cl, 4-F-Phenoxy) | H | 7.75(1H); 7.65(1H); 7.45 (2H); 7.4-6.9(10H); 3.8(3H); 3.65(3H) |
| 2.016 | 4-(Pyrid-3-yl) | H | 8.9(1H); 8.6(1H); 7.9-7.1(13H); 3.75(3H); 3.65(3H) |
| 2.017 | 4-(Thienyl-3-yl) | H | 7.75-7.0(14H); 3.8(3H); 3.65(3H) |
| 2.018 | 4-Imidazolyl | H | 7.9-7.0(14H); 3.8(3H); 3.65(3H) |
| 2.019 | 3-Phenyl | H | 7.8-7.0(16H); 3.8(3H); 3.65(3H) |

Examples of Use

The insecticidal action of the compounds of the general formula I' could be demonstrated by the following experiments:

The active ingredients were prepared
a) as a 0.1% strength solution in acetone or
b) as a 10% strength emulsion in a mixture of 70% by weight of cyclohexanol, 20% by weight of Nekanil ® LN (Lutensol ® AP6, wetting agent having an emulsifying and dispersing action and based on ethoxylated alkylphenols) and 10% by weight of Emulphor ® EL (Emulan ®, emulsifier based on ethoxylated fatty alcohols) and were diluted with acetone in the case of a) and with water in the case of b), according to the desired concentration.

After the end of the experiments, the lowest concentration in each case at which the compounds still caused an 80–100% inhibition or kill rate compared with untreated control experiments was determined (action threshold or minimum concentration).

A. Aphis fabae (bean aphid), contact action

Highly infested bushbeans (*Vicia faba*) were treated with the dqueous active ingredient formulation.

The kill rate was determined after 24 hours.

In this test, compounds 2.013, 2.014, 2.015, 2.016 and 2.019 had action thresholds of from 200 to 1,000 ppm.

B. *Musca domestica* (house fly), breeding experiment 25 ml of a dry feed mixture (1 kg of bran, 250 g of yeast powder and 35 g of fish meal) were mixed with the active ingredient and 25 ml of a milk/sugar solution (1 l of milk and 42 g of sugar) and then infested with 30 larvae in the first stage of development (LI).

After hatching of the larvae in a control experiment without active ingredient, the kill rate was determined.

In this test, compounds 2.005, 2.006, 2.013, 2.014, 2.015 and 2.016 had action thresholds of from 10 to 100 ppm.

C. *Plutella maculipennis* (diamondback caterpillar), contact action

The leaves of young cabbage plants were wetted with the aqueous active ingredient formulation and then placed on a moistened filter. The prepared leaves were then each infested with 10 caterpillars in the fourth stage of development.

The kill rate was determined after 48 hours.

In this test, compounds 2.002, 2.003, 2.005, 2.006, 2.009, 2.011, 2.012, 2.013, 2.014, 2.015, 2.016 and 2.019 had action thresholds of from 100 to 400 ppm.

D. *Tetranycus telarius* (red spider mite), contact action

Severely infested potted bush beans which had the second pair of secondary leaves were sprayed to run-off with aqueous active ingredient formulation.

After 5 days in a greenhouse, the success of control was determined using a binocular microscope.

In this test, compounds No. 1.002, 1.003, 1.004, 1.005, 2.007, 2.008, 2.013 and 2.019 had action thresholds of less than 200 to 1,000 ppm.

The fungicidal action of the compounds of the general formula I could be demonstrated by the following experiment:

The active ingredients were prepared as an aqueous spray liquor which contained 80% of active ingredient and 20% of emulsifier, the percentages being based on dry substance. The active ingredient A disclosed as Example No. 1 in EP-A 203 606

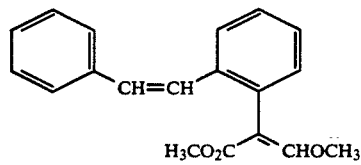

(A)

served as the comparative compound.

*Puccinia recondita* (wheat brown rust)

Wheat seedlings of the Fruhgold variety which had been dusted with Puccinia recondita spores were incubated for 24 hours at from 20° to 22° C. and from 90 to 95% humidity. The plants pretreated in this manner were treated with the aqueous active ingredient formulation.

After 8 days in the greenhouse, the success of control was determined in comparison with an untreated control.

In this experiment, considerably better control was achieved with compounds 1.002, 1.003, 1.004, 1.005, 2.002, 2.005 and 2.008 than with comparative compound A.

We claim:

1. An α-arylacrylic acid derivative of the formula

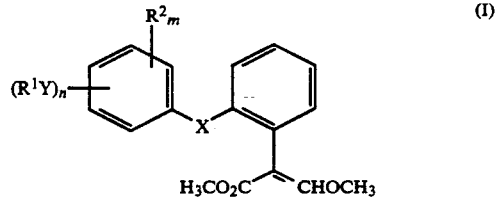

(I)

where

X is ethylene or ethylene;

Y is a direct bond or oxygen;

R¹ is a mononuclear or dinuclear aromatic system which is bonded via a carbon atom, and this aromatic system is optionally substituted by from one to seven halogen atoms or from one to four of the following radicals: $C_1$-$C_4$-alkyl, $C_1$-$C_4$-haloalkyl, $C_1$-$C_4$-alkoxy, $C_1$-$C_4$-halozlkoxy, $C_1$-$C_4$-alkythio, $C_1$-$C_4$-haloalkythio, $C_3$-$C_6$-cycloalkyl, $C_5$-$C_6$-cycloalkenyl, $C_2$-$C_4$-alkenyl or $C_2$-$C_4$-alkynyl or from one to three cyano or nitro substituents; R² is cyano, nitro, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, or $C_1$-$C_4$-haloalkylthio; n is 1 or 2, and the substituents are identical or different if n is 2, and m is 1, 1 or 2, and the substituents are identical or different if m is 2, with the proviso that R¹ is not phenyl or alkylphenyl when n is 1 and m is 0.

2. A pesticide or fungicide composition comprising an effective amount of an α-arylacrylic acid derivative of the formula I as defined in claim 1 and inert carrier.

3. A method for controlling fungi, wherein the fungi or their habitat are or is treated with an effective amount of an α-arylacrylic acid derivative of the formula I as defined in claim 1.

4. A method for controlling insects, arachnids or nematodes, wherein the insects, arachnids or nematodes or their habitat are or is treated with an effective amount of an α-arylacrylic acid derivative of the formula I'

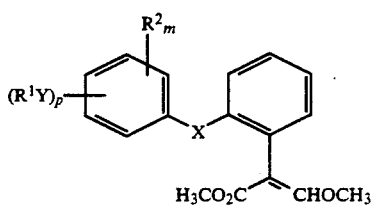

(I')

wherein

X is ethylene or ethenylene;

Y is a direct bond or oxygen;

$R^1$ is a mononuclear or dinuclear aromatic system which is bonded via a carbon atom, and this aromatic system is optionally substituted by from one to seven halogen atoms or from one to four of the following radicals; $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_5$- or $C_6$-cycloalkenyl, $C_2$-$C_4$-alkenyl or $C_2$-$C_4$-alkynyl or from one to three cyano or nitro substituents;

$R^2$ is cyano, nitro, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkythio, or $C_1$-$C_4$-haloalkythio; n is 1 or 2, and the substituents are identical or different if n is 2, and m is 0, 1 or 2, and the substituents are identical or different if m is 2, with the proviso that $R^1$ is not phenyl when X is ethylene, X is oxygen, p is 1 and m is 0.

* * * * *

UNITED STATES PATENT AND TRADEMARK OFFICE
CERTIFICATE OF CORRECTION

PATENT NO. : 5,294,639
DATED : Mar. 15, 1994
INVENTOR(S) : KIRSTGEN et al.

It is certified that error appears in the above-indentified patent and that said Letters Patent is hereby corrected as shown below:

IN THE CLAIMS

Claim 1, column 18:

line 22, "ethylene", second occurrence, should read --ethenylene--.

line 29, delete "$C_1$-$C_4$-halozlkoxy, $C_1$-$C_4$-alkythio," and substitute --$C_1$-$C_4$-haloalkoxy, $C_1$-$C_4$-alkylthio--.

line 30, delete "$C_1$-$C_4$-haloalkythio" and substitute --$C_1$-$C_4$-haloalkylthio--.

line 30 bridging line 31, delete "$C_5$-$C_6$-cycloalkenyl" and substitute --$C_5$- or $C_6$-cycloalkenyl--.

line 38, delete "1", first occurrence, and substitute --0--.

Claim 4, column 20, line 9, delete "X" and substitute --Y--.

Signed and Sealed this

Nineteenth Day of July, 1994

Attest:

BRUCE LEHMAN

*Attesting Officer*   *Commissioner of Patents and Trademarks*